(12) United States Patent
Wang et al.

(10) Patent No.: US 6,991,715 B2
(45) Date of Patent: Jan. 31, 2006

(54) PRION DIAGNOSTIC TEST

(75) Inventors: Kailing Wang, Carlingford (AU); Chenicheri Hariharan Nair, Old Greenwich, CT (US)

(73) Assignee: Gradipore Limited, Frenchs Forest (AU)

( * ) Notice: Subject to any disclaimer, the term of this patent is extended or adjusted under 35 U.S.C. 154(b) by 367 days.

(21) Appl. No.: 10/146,596

(22) Filed: May 15, 2002

(65) Prior Publication Data

US 2003/0000836 A1 Jan. 2, 2003

(30) Foreign Application Priority Data

May 15, 2001 (AU) .................... PR 5015
Jul. 4, 2001 (AU) .................... PR 6100

(51) Int. Cl.
*G01N 27/447* (2006.01)
*G01N 33/53* (2006.01)
*G01N 33/68* (2006.01)

(52) U.S. Cl. ............... 204/548; 204/450; 204/518; 435/7.92

(58) Field of Classification Search ........... 204/450, 204/548, 600, 644, 518, 519, 627, 628; 435/5, 435/7.92, 7.93, 7.94, 975, 962
See application file for complete search history.

(56) References Cited

U.S. PATENT DOCUMENTS 3,870,617 A * 3/1975 Boural .................. 204/633
5,039,386 A 8/1991 Margolis
6,660,150 B2 * 12/2003 Conlan et al. .......... 204/627

FOREIGN PATENT DOCUMENTS

| WO | WO 00/13776 A1 | 3/2000 |
| WO | WO 00/38743 A1 | 7/2000 |
| WO | WO 00/40966 A1 | 7/2000 |
| WO | WO 01/10470 A1 | 2/2001 |
| WO | WO 01/78878 A1 | 10/2001 |

OTHER PUBLICATIONS

Prusiner, S.B., "Prions", Proc. National Acad. Sci., Nov. 10, 1998 Abstract only.
Fischer, M.B. et al., "Binding of disease-associated prion protein to plasminogen", Nature, Nov. 23, 2000, pp. 479-483 Abstract only.
Brown P. et al., "Blood infectivity and the prospects for a diagnostic screening test in Creutzfeldt-Jakob disease", J. Lab Clin Med, Apr. 2001 Bibliography only.
Yokoyama, T. et al., "In Vivo Conversion of Cellular Prion Protein to Pathogenic Isoforms, as Monitored by Conformation-specific Antibodies", J. Biol. Chem., vol. 276, Issue 14, pages Abstract only.
MacGregor I., "Prion protein and developments in its detection", Transfus Med., Feb. 2001 Abstract only.
MacGregor I. et al., "Distribution of normal prion protein in blood", Elsevier Scient, Feb. 2000 Bibliography only.

(Continued)

*Primary Examiner*—Kaj K. Olsen
(74) *Attorney, Agent, or Firm*—Morgan, Lewis & Bockius LLP (57) ABSTRACT

The claims provide for detecting prions in a sample by (a) subjecting a sample to membrane-based electrophoresis to separate and/or concentrate at least some prions present in the sample; and (b) detecting and or identifying the presence of the separated and/or concentrated prions.

27 Claims, 6 Drawing Sheets

OTHER PUBLICATIONS

MacGregor I. et al., "Application of a time-resolved fluoroimmunoassay for the analysis of normal prion protein in human blood and its components", Karger, Vox Sang 1999, Abstract only.

Horvath, Stephen Z. et al., "Multifunctional Apparatus for Electrokinetic Processing of Proteins", Electrophoresis 1994, vol. 15, pp. 968-971.

* cited by examiner

SDS-PAGE              Western Blot

Lane 1:   MW
Lane 2:   bovine brain tissue homogenates
Lane 3:   human plasma
Lane 4:   negative control-no antibody was added (protein A agarose)
Lane 5:   negative control-no antibody was added (protein G agarose)
Lane 6:   anti-PrP treated sample (protein A agarose)
Lane 7:   anti-PrP treated sample (protein G agarose)

Step 1: charged-based

MW S1₀ S1₁₈₀ S2₀ S2₆₀ S2₁₂₀ S2₁₈₀

Step 2: size-based/concentration

SDS-PAGE

A

S1₀ S1₁₈₀ S2₀ S2₁₈₀  S1₀ S1₁₈₀ S2₀ S2₁₈₀

Western Blot

PRION DIAGNOSTIC TEST

CROSS-REFERENCE TO RELATED APPLICATIONS

This application claims benefit of the Australian Provisional Application Nos. PR5015 filed May 15, 2001 and PR6100 filed Jul. 4, 2001.

FIELD

The present application relates to tests for the detection of infectious agents, particularly an assay for the detection of prions in samples using membrane-based electrophoresis.

BACKGROUND

Bovine spongiform encepalopathy (BSE), scrapie of sheep, Kuru and Creutzfeldt-Jakob disease (CJD) of humans are only a few examples of a group of neurodegenerative disorders named transmissible spongiform encepalopathies (TSE) which are characterized by loss of motor control, dementia, paralysis, blindness, wasting and eventually death. These diseases may be inherited or sporadic. A risk of contracting TSE for humans is believed to be through food products derived from BSE-infected cattle. Another transmission risk is possible infection through human blood and blood products which originated from TSE-infected donors.

Recently, it was shown that these fatal neurodegenerative diseases are caused by a newly discovered infectious pathogen named prion protein (PrP) (Prusiner S. B., *P.N.A.S.* 95, 13363–13383, 1998). More precisely, the accumulation of an infectious isoform of PrP into amyloid plaques results in the development of the disease. Different isoforms of PrP have been identified as a normal cellular form ($PrP^c$) and a highly infectious scrapie form ($PrP^{Sc}$). The $PrP^{Sc}$ form of the protein was found to be protease and detergent resistant, while $PrP^c$ has been shown to be sensitive to the conventional treatment processes causing protein degradation and denaturation. Although identical in amino acid sequence, the two proteins have been shown to have different conformational characteristics with $PrP^c$ containing more α-helical structure than its infectious counterpart. Nevertheless, there has been no effective method of discriminating between the two proteins by the way of immunoreagents. Only recently, plasminogen was recognized as the first naturally occurring $PrP^{Sc}$-binding protein that can distinguish between $PrP^c$ and $PrP^{Sc}$ (Fischer M. B., *Nature*, 406, 479–483, 2000).

A handful of blood-screening test methods are in different stages of development. Several methods appear to have threshold PrP detection sensitivities within the range of what might be encountered in the blood of infected individuals, but none has yet been shown to be capable of detecting $PrP^{Sc}$ in the blood of human beings who are incubating CJD (Brown et al., *J. Lab. Clinic. Med.* 137 (1), 5–13, 2001). In addition, the methods and instruments used for detection have two critical limitations: inherent insensitivity of the method and a minimum specimen volume to be tested by the instrument.

Currently, there are no commercial non-invasive assays that allow detection of prions in infected individuals prior to the development of clinical symptoms of disease. The few tests that are in use are able to detect prions in brain tissue and the spinal cord only and are largely used on animals and humans in their post-mortem state.

In the pre-clinical phase of prion infection in experimentally infected rodents, it was identified that $PrP^{Sc}$ infectivity was closely associated with blood buffy coat, leucocyte, platelet and plasma fractions.

SUMMARY

The present application provides for methods, kits, and assays for detecting prions in a sample using membrane-based electrophoresis.

Briefly, a method, kit or assay subjects a sample to membrane-based electrophoresis to separate and/or concentrate at least some prions present in the sample, and detects the presence of the separated and/or concentrated prions. The sample may be any liquid sample suitable for undergoing electrophoresis.

These and other features of the present application will be appreciated from review of the following detailed description of the application along with the accompanying figures.

DETAILED DESCRIPTION

Preferred embodiments of detecting prions in a sample according to the present application are described in non-limiting detail below.

Figure 1:
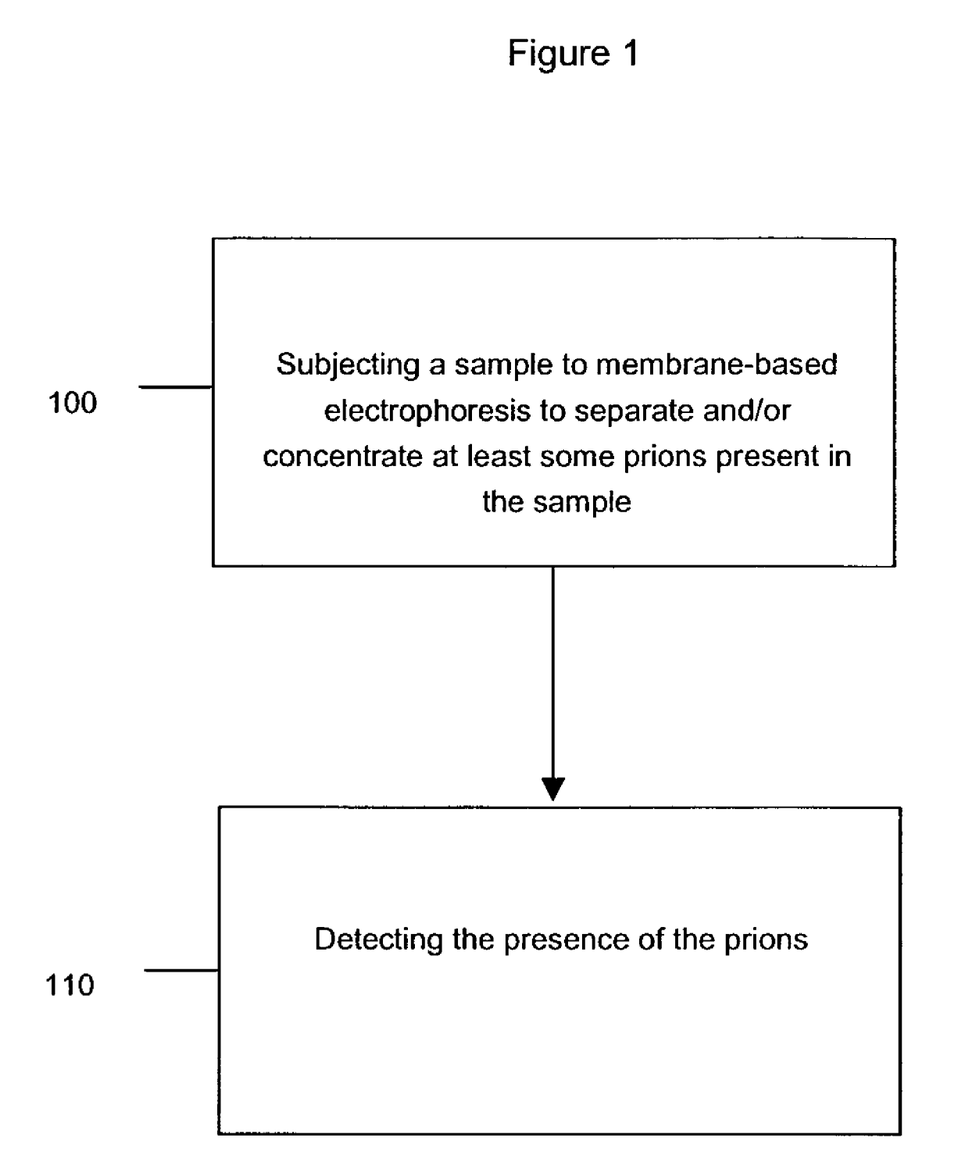
FIG. 1 is a block diagram of a method, kit, or assay for detecting prions in a sample practiced according to the present application.
Figure 2:
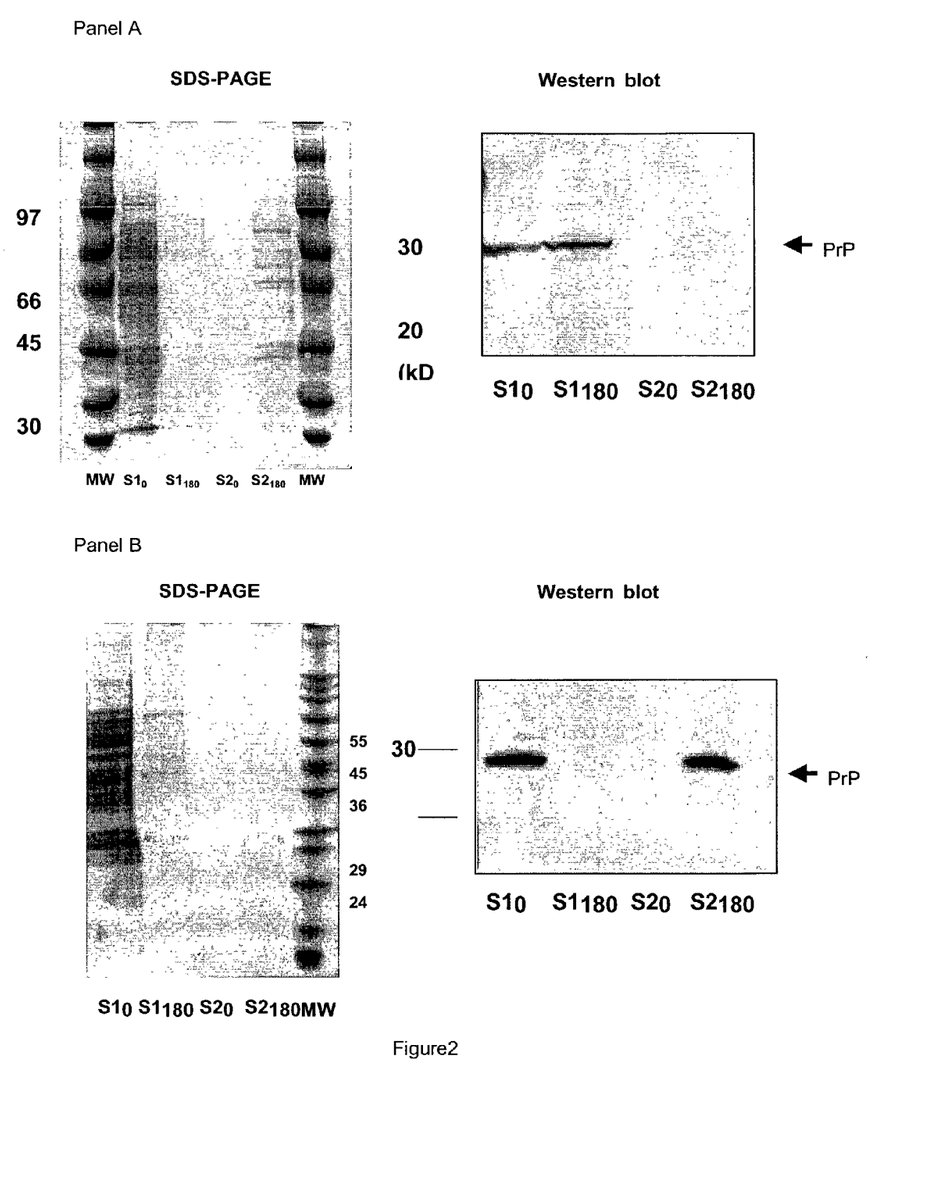
FIG. 2 is an SDS-PAGE and Western Blot analysis of bovine $PrP^c$ as described in Example 1. Panel A depicts an SDS-PAGE and Western Blot of sample aliquots removed from both Stream 1 and Stream 2. Panel B depicts an SDS-PAGE and Western Blot of sample aliquots removed from both Stream 1 and Stream 2.
Figure 3:
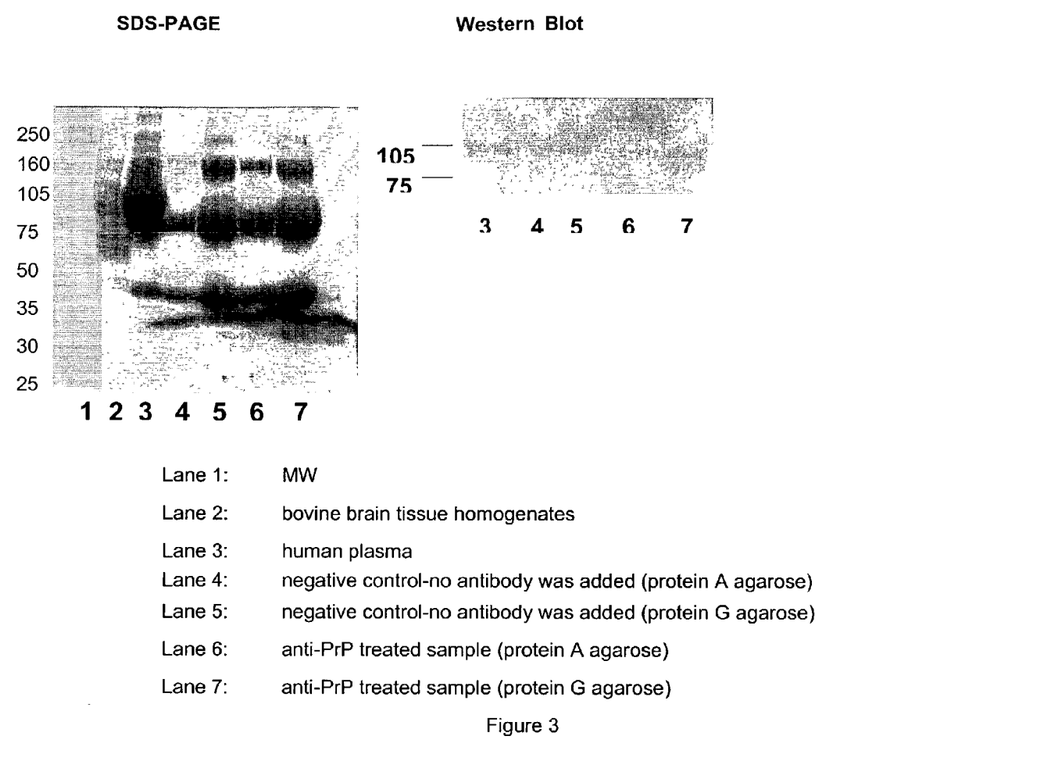
FIG. 3 is an SDS-PAGE and Western Blot analysis of bovine $PrP^c$ as described in Example 2.

FIG. 1 refers to a block diagram of a method, kit, or assay for detecting prions in a sample practiced according to the present application. Block 100 depicts subjecting a sample to membrane-based electrophoresis to separate at least some prions present in the sample. The sample in block 100 may be any liquid sample suitable for undergoing electrophoresis. For example, the sample may be a biological sample including blood, plasma, serum, blood, cell products or extracts, cerebrospinal fluid (CSF), tissue homogenates, urine, semen or combinations thereof. However, other liquid samples known in the art that may be electrophoresed may also be used.

In one embodiment, electrophoresis separates at least some prions present in the sample. In another embodiment, electrophoresis concentrates at least some prions present in the sample. In yet another embodiment, electrophoresis separates and concentrates at least some prions present in the sample. For example, the sample in block 100 may be separated and concentrated to contain at least some prions in a smaller volume.

The electrophoresis in block 100 may be performed on a membrane-based electrophoresis apparatus. In one embodiment, a small electrophoresis apparatus having static chambers is used for subjecting a sample to membrane-based electrophoresis in block 100. In this particular embodiment, a sample is applied to a sample chamber of an electrophoresis apparatus adapted to receive small volumes comprising a static cathode compartment, a static anode compartment, an electrophoresis separation membrane having a defined pore size and pore size distribution disposed between the anode and cathode compartments, a first restriction membrane disposed between the cathode compartment and the separation membrane so as to define a sample chamber having a small interstitial volume, and a second restriction membrane disposed between the anode compartment and the separation membrane so as to define a separation chamber having a small interstitial volume, wherein recirculation of liquid in the compartments or chambers is minimized. An electric potential is applied to the sample in the sample chamber such that prions in the sample move toward the separation membrane and preferably pass through the membrane into the separation chamber, or such that components other than prions in the sample move toward the separation membrane and preferably pass through the membrane into the separation chamber. In another embodiment, the electrophoresis apparatus contains a cathode positioned in the cathode compartment and an anode positioned in the anode compartment. To contain prions in the sample and/or separation chambers, the restriction membranes minimize movement of prions to the respective electrode compartments.

In one embodiment, the small interstitial volume is less than about 10 ml, preferably about 5 ml or less. A static fluid apparatus is particularly suitable for separating samples of about 1 to about 0.02 ml. Larger volumes may be processed depending on the configuration of the electrophoresis apparatus used.

A ratio of sample to separation membrane surface area of less that about 5 ml/cm$^2$ or even 1 ml/cm$^2$ is preferred. Preferably, the ratio is 0.5 ml/cm$^2$ or less, more preferably the ratio is 0.1 ml/cm$^2$ or less, and even more preferably around 0.02 ml/cm$^2$.

A small electrophoresis apparatus is suitable for testing a number of samples, for example, in arrays or multi-well plates. In another embodiment, block 100 is automated by using an electrophoresis apparatus capable of running a number of samples which would be deposited on multi-well plates (e.g., pre-coated with a selective PrP-binding agent) for further prion concentration or detection.

The electrophoresis apparatus may have other configurations, e.g., where the anode and cathode compartments are reversed. In this form, the sample chamber is disposed adjacent the anode compartment and the separation chamber is disposed adjacent the cathode compartment. Reversing the polarity of the electrodes also practices embodiments of the claims. Examples of other small electrophoresis apparatus suitable for use in the present invention may be found in WO 01/78878, incorporated herein by reference.

In another embodiment, block 100 is carried out using an electrophoresis apparatus containing a separation unit having a first electrolyte chamber in fluid connection with an electrolyte reservoir, a second electrolyte chamber in fluid connection with the electrolyte reservoir, a first sample chamber being in fluid connection with a first sample reservoir, and a second sample chamber being in fluid connection with a second sample reservoir; a first ion-permeable barrier, wherein the first ion-permeable barrier minimizes convective mixing of contents of the first and second sample chambers; a second ion-permeable barrier, wherein the second ion-permeable barrier minimizes convective mixing of contents of the first electrolyte chamber and the first sample chamber; a third ion-permeable barrier, wherein the third ion-permeable barrier minimizes convective mixing of contents of the second electrolyte chamber and the second sample chamber; supplying electrolyte from the electrolyte reservoir to the first electrolyte chamber and the second electrolyte chamber; and supplying sample or liquid from at least the first sample reservoir to the first sample chamber, or from the second sample reservoir to the second sample chamber; wherein the supplying steps are performed before the detecting step in block 110. Description of membrane-based electrophoresis apparatus of this type may be found in U.S. Pat. Nos. 5,093,386 and/or 5,650,055, which are incorporated herein by reference.

In one embodiment, the first ion-permeable barrier is positioned between the first sample chamber and the second sample chamber. In another embodiment, the second ion-permeable barrier is positioned between the first electrolyte chamber and the first sample chamber. In another embodiment, the third ion-permeable barrier positioned between the second sample chamber and the second electrolyte chamber.

In one embodiment, the first ion-permeable barrier is a membrane having a defined average pore size and pore size distribution. In another embodiment, all the ion-permeable barriers are membranes having a defined average pore size and pore size distribution. This configuration of the apparatus is suitable for separating on the basis of charge and/or size.

In another embodiment, the electrophoresis apparatus of block 100 circulates contents from each of the first and second sample reservoirs through the respective first and second sample chambers forming first and second sample streams in the respective sample chambers. For example, in one embodiment, a pump arrangement controls movement of the sample streams. Of course, other circulating arrangements known in the art may also be used.

In another aspect, the electrophoresis apparatus used in block 100 removes and replaces sample in the first or second sample reservoirs, maintains temperature of electrolyte and sample solutions, or any combinations thereof.

In another embodiment, the separation unit is provided as a cartridge or cassette housing the ion-permeable barriers fluidly connected to the electrolyte reservoirs and the sample reservoirs.

In one aspect, a sample is placed in the first or second sample reservoirs and provided to, or circulated through, the first or second chambers. The sample may also be placed in both the first or second sample reservoir or in either the first or second sample reservoirs. Likewise, the sample may then be circulated through both the first and second chambers or through just one of either the first or the second chambers. Electrolyte is placed in the electrolyte reservoir and passed to, or circulated through, the first and second electrolyte chambers. Electrolyte or other liquid may also be placed in the first and/or second sample reservoirs. An electric potential is applied to the electrodes wherein one or more components in the first and/or second sample chamber are caused to move through an ion permeable barrier to the second and/or first sample chamber, or to the first and/or second reservoir chambers according to electrophoretic principles. Treated sample or components separated from the sample may be collected in the second and/or first sample reservoir.

In one embodiment, a cathode zone and an anode zone are supplied with suitable buffer solutions by any suitable pumping arrangement. A sample to be processed is supplied directly to the first or second interstitial volumes by any suitable pumping arrangement.

In another embodiment, the anode and cathode zones and the first and second streams are configured to allow flow of the respective fluid/buffer and sample solutions forming streams. In this way, larger volumes may be processed quickly and efficiently. The solutions are typically moved or recirculated through the zones and streams from respective reservoirs by suitable pumping arrangements. For example, peristaltic pumps may be used as the pumping arrangement for moving the sample, buffers or fluids. However, other suitable pumping arrangements known in the art may also be used.

In one embodiment, the buffer and sample solutions are cooled by any suitable cooling arrangement to minimize inactivation of sample constituents during the separation process and to maintain a desired temperature of the apparatus while in use. Suitable cooling arrangements are readily known to practitioners in the art.

In order to collect and/or concentrate separated constituents, solution in at least one of the streams containing any separated compounds or molecules is collected and replaced with suitable solvent to ensure that electrophoresis continues.

It will be appreciated that this procedure may also be reversed where a sample is placed in the second solvent stream, the polarity of the electrodes being reversed so the product is collected in the first solvent stream. In some applications, the sample may be placed in either the first or second solvent stream and the prions moved to the opposite stream by electrophoretic principles during electrophoresis in block 100. Alternatively, the prions are caused to remain in the original stream while other components are removed from the sample into the other solvent stream according to electrophoretic principles during electrophoresis in block 100.

In one embodiment, the first ion-permeable barrier is an electrophoresis separation membrane that is comprised of polyacrylamide and has a defined molecular mass cut-off. For example, one electrophoresis separation membrane has a molecular mass cut-off up to about 1500 kDa. A molecular mass cut off of about 1000 kDa is also suitable for the electrophoresis separation membrane. It will be appreciated, however, that other membrane chemistries or constituents may also be used. For example, other cut-off membranes that allow for movement of prions or other components in samples being processed are also suitable. The selection criteria for these other membranes utilized during electrophoresis is readily known to practitioners in the electrophoretic art.

The second and third ion-permeable barriers may be restriction membranes. For example, in one embodiment, these barriers are formed from polyacrylamide, and have a molecular mass cut-off less than the separation membrane, preferably from about 1 kDa to about 500 kDa. The molecular mass cut-off of the restriction membrane will depend on the sample being processed and the size of the components to be removed or retained. The selection criteria are readily known in the art. In one embodiment, the molecular mass cut-off of the restriction membranes is less than the molecular mass cut-off of the separation membrane.

In another embodiment, at least one membrane forming the ion permeable barriers is capable of controlling bulk movement of liquid under the influence of an electric field. For example, an inducible electro-endo-osmotic membrane may be used. The inducible electro-endo-osmotic membrane may be a poly-vinyl alcohol (PVA) membrane or a cellulose tri-acetate (CTA) membrane. For example, a PVA membrane having a nominal molecular mass cut-off of 20–50 kDa is suitable for use in the apparatus according to the present application.

In one embodiment, first ion-permeable barrier is an electrophoresis membrane having a molecular mass cut-off of about 1000 kDa and the second and third ion-permeable barriers are restriction membranes having a molecular mass cut-off of about 10 kDa. In another embodiment, the first ion-permeable barrier is an electrophoresis membrane having a molecular mass cut-off of about 100 kDa, the second ion-permeable barrier is an inducible electro-endo osmotic membrane, and the third ion-permeable barrier is a restriction membrane having a molecular mass cut-off of about 10 kDa. It will be appreciated that other molecular mass cut-offs would also be suitable for the present invention. It will also be appreciated that the inducible electro-endo-osmotic membrane can also be formed from cellulose tri-acetate (CTA) or any other suitable membrane material known in the art.

In another embodiment, electrophoresis separation membrane of about 1000 kDa and two restriction membranes of about 10 kDa are suitable for prion processing according to the present application. Depending on the pH of the sample and electrophoresis buffer, the prions may be negatively charged, positively charged or have no charge. Movement of prions (and other compounds in a sample) by electrophoresis will depend on the charge and size of the prions and/or any other compounds in the sample to be processed. By selecting the buffer and molecular mass cut off of the separation and restriction membranes, various separations of prions and other compounds in a given sample may be performed according to electrophoretic principles known in the art.

Voltage and/or current applied may also vary depending on the separation. Typically, several hundred volts may be used, but choice and variation of voltage will depend on the configuration of the apparatus, buffers and the sample to be separated or treated. In a laboratory scale instrument, the preferred voltage is about 250 V. However, other voltages 
may be used, and the selection criteria for the amount of voltage and/or current in view of apparatus configuration, the type of buffer and sample composition is readily known without undue experimentation to one skilled in the art.

Still referring to FIG. 1, block 110 detects the prions that have been separated and/or concentrated in block 100. For example, block 110 may use a prion capture system utilizing a selective agent that selectively binds infectious prions ($PrP^{Sc}$) and that may also be used to detect and distinguish infectious prions from normal prions. In this mode, both $PrP^c$ and $PrP^{Sc}$ may be recovered by the electrophoresis step in block 100 and detection and discrimination between $PrP^c$ and $PrP^{Sc}$ is made by using a selective binding agent in block 110. In one embodiment, the selective binding agent is immobilized on a support matrix. For example, Agarose beads, 96-well plates, or other support matrices known in the art may be used.

The selective agent may be a biological or chemical agent that selectively binds prions, for example, an agent that selectively binds to infectious prions rather than to normal prions or, as another example, an agent that selectively binds to normal prions rather than to infectious prions. The biological agent may be proteins, peptides, small molecules, antibodies, binding fragments of antibodies, plasma components, plasminogen, angiostatin, fibrin, fibrinogen or combinations thereof. However, other biological agents that selectively bind either normal or infectious prions may also be used. For example, conformation-specific antibodies (Yokoyama et al. Journal of Biological Chemistry, 276(14), 11265–11271) and epitope-specific antibodies described in O'Rourke et al. (U.S. Pat. No. 6,165,784) and incorporated by reference herein may be used in the detecting step in block 110.

As another example, the chemical agent may be a heteropoly acid or salts thereof. The heteropoly acid may be, for example, phosphotungstic acid or salts thereof as disclosed in U.S. Pat. No. 6,166,187, and incorporated by reference herein. Of course, other suitable chemical agents or other heteropoly acids (or salts thereof) that selectively bind to prions may also be used.

One embodiment detects the presence of infectious prions $PrP^{Sc}$ in a sample. Another embodiment detects the presence of normal prions $PrP^{c}$. In another embodiment, block 110 distinguishes the presence of $PrP^{Sc}$ from $PrP^{c}$.

In one aspect, block 110 characterizes the physical or biochemical properties of the prions. For example, block 110 may characterize the properties of infectious prions in the sample. Alternatively, block 110 may characterize the properties of the normal prions in the sample. As one example, block 110 may measure the solubility, three-dimensional structure, Circular Dichroism (CD), hydrophobicity, infectivity, pI value, or other physical and biochemical properties of prions in the sample. Of course, other physical or biochemical properties known in the art may be measured according to the present application.

In another aspect, block 110 may use an immuno-detection assay. For example, the immuno-detection assay may be an enzyme linked immunosorbant assay (ELISA), Western Blot, time resolved dissociation-enhanced fluoroimmunoassay (DELFIA), radioimmunoassay, or any other immunoassay known in the art.

The embodiments referred to in FIG. 1 may be used in a variety of different ways, for example, as kits, assays, and methods of separating prions from other components in a sample. As another example, embodiments may be used to separate and/or distinguish normal prions from infectious prions. As prions are usually present in very low concentrations in samples and are therefore extremely difficult to detect, embodiments may also be used to concentrate prions in the sample or the separation chamber by removing other components in the sample, or selectively separating the prions from the sample, or by transferring prions from a large volume to a smaller volume.

One embodiment uses a $PrP^{Sc}$-selective binding agent (e.g., plasminogen, anti-$PrP^{Sc}$ antibody, angiostatin, fibrin, fibrinogen or chemical agent) chemically-immobilized on a support matrix (e.g., Agarose beads or 96 well plates). $PrP^{Sc}$ in the sample following separation are captured and concentrated by the immobilized matrix and subsequently may be detected by Western Blot, ELISA, DELFIA, or any other known analytical method. Thus, a diagnostic assay may be used to detect prions and prion infectivity in blood or other biological samples.

As another example, electrophoresis separation may be used to at least partially separate PrP from blood fractions such as plasma and platelets. A selective binding agent (e.g., plasminogen, angiostatin, fibrin, fibrinogen or $PrP^{Sc}$-specific antibody) immobilized onto a support matrix is used to identify and concentrate the $PrP^{Sc}$ in the treated sample after electrophoresis separation. $PrP^{Sc}$ can then be treated with proteinase K, for example, and subsequently detected by Western Blot using a specific anti-prion antibody. In this manner, detection of prions in whole blood may be used for preclinical diagnosis since prions circulate in small amounts in infected individuals.

In another embodiment, an electrophoresis separation apparatus may be modified so that the samples from the separation chamber can flow or be deposited to a 96-well $PrP^{Sc}$ selective binding agent (e.g., plasminogen, angiostatin, fibrin, fibrinogen or $PrP^{Sc}$-specific antibody)-immobilized plates. Following the separation, $PrP^{Sc}$ may be detected, for example, by ELISA or DELFIA using a specific anti-prion antibody or by radioimmunoassay for example.

In one embodiment, plasminogen (or, e.g., angiostatin, fibrin, fibrinogen or another macro or micromolecule or particle or $PrP^{Sc}$-specific antibody) is coated to the separation membrane before plasma or platelet samples are subjected to electrophoretic separation. Prion protein remaining in samples may be analyzed by Western Blot, ELISA, DELFIA, or other suitable analytical method known in the art after its subsequent dissociation from the membrane by addition of denaturing reagent.

A distinct advantage of an embodiment practiced according to the present application stems from the ability to perform prion separation with a small volume of blood fractions. For example, a $PrP^{Sc}$-specific binding matrix (e.g., plasminogen, angiostatin or antibodies) identifies and concentrates $PrP^{Sc}$ for further detection of, for example, prion diseases such as BSE and vCJD in symptom-free animals and humans and potentially clear the pathological prions from blood products. In another aspect, embodiments may also include automated arrangements that provide for high throughput screening, or diagnosis operations. For example, either or both blocks 100 and 110 may contain automated components.

To assist in understanding the present application, the following examples are included and describe the results of a series of experiments. The following examples relating to this application should not be construed to specifically limit the application or such variations of the application, now known or later developed, which fall within the scope of the application as described and claimed herein.

Experimental Conditions Apparatus A number of membrane-based electrophoresis apparatus obtainable from Gradipore Limited, Australia were used in the following experiments. In summary, the apparatus typically included a cartridge, which houses a number of membranes forming two chambers, cathode and anode connected to a suitable power supply, reservoirs for samples, buffers and electrolytes, pumps for passing samples, buffers and electrolytes, and cooling means to maintain samples, buffers and electrolytes at a required temperature during electrophoresis.

The cartridge contained three substantially planar membranes positioned and spaced relative to each other to form two chambers through which sample or solvent may be passed. A separation membrane is positioned between two outer membranes (termed restriction membranes as their molecular mass cut-offs are usually smaller than the cut off of the separation membrane). When the cartridge is installed in the apparatus, the restriction membranes are located adjacent to an electrode. The cartridge is described in AU 738361, and is incorporated herein by reference.

As noted above, description of a membrane-based electrophoresis apparatus may be found in U.S. Pat. Nos. 5,039,386 and/or 5,650,055, and are incorporated herein by reference.

Samples

Normal prion protein ($PrP^c$) samples from either bovine brain tissue homogenates or human plasma were used in all experiments. As infectious prion protein ($PrP^{Sc}$) is difficult to obtain, $PrP^c$ samples were used. It will be appreciated that the results obtained with $PrP^c$ should be applicable to samples containing $PrP^{Sc}$.

Separation Conditions

Using human plasma as a starting material, size-based separation of normal prion protein ($PrP^c$) was performed followed by a charge-based separation. The amount of prion protein in human plasma was quantified by a time-resolved dissociation-enhanced fluoroimmunoassay DELFIA (EG&G Wallac). All samples generated from the electrophoresis runs were analyzed by SDS-PAGE for protein separation. Based on the characteristics of human plasma prion protein, a 2-step separation process was developed to remove plasma protein contaminants and to purify prion protein. This was followed with a simultaneous separation and concentration of human plasma PrP by utilizing PVA electro-endo-osmotic (EEO) membranes. $PrP^c$ present in these samples were quantified by DELFIA assay (EG&G Wallac).

Separation of $PrP^c$ from Bovine Brain Homogenate

Using normal bovine prion protein ($PrP^c$) as a surrogate for the abnormal form associated with TSE infectivity, conditions have been established for membrane-based electrophoresis to separate or retain prion protein from or in bovine brain tissue homogenates, thus allowing for the capture, purification and removal of prions. In addition, a simultaneous separation and concentration of prion protein from bovine brain homogenate was achieved by utilizing electro-endosmostic (EEO) membrane.

EXAMPLE 1

Separation of $PrP^c$ from bovine brain homogenate was carried out for 3 hours at 250V using a cartridge with a separation membrane of 150 kDa and two restriction membranes of 10 kDa. When 20 mM Tris Borate buffer (pH 9.0) was used during electrophoresis, $PrP^c$ remained in the sample chamber (see Panel A of FIG. 2). By changing the electrophoresis conditions (e.g. reverse polarity), $PrP^c$ was completely transferred to the separation chamber under same membrane configurations and voltage conditions but with 30 mM GABA/Acetic Acid buffer (pH 4.6) (Panel B of FIG. 2). $S1_0$ is Stream 1 at time 0 minutes, $S1_{180}$ is Stream 1 at time 180 minutes, $S2_0$ is Stream 2 at time 0 minutes, $S2_{180}$ is Stream 2 at time 180 minutes. As shown in FIG. 2 (Panel A and B), the bovine prion protein can either be completely transferred from the sample material in the first stream to the second stream or retained in the first stream after electrophoresis separation. The results show that electrophoresis successfully separates or retains prions from or in samples. The electrophoresis step enables the capture and partial purification of prions.

EXAMPLE 2

A mixture of human plasma and bovine brain homogenate (1:3 v/v) was incubated with anti-PrP antibody at room temperature for 2 hours to allow plasminogen/PrP immunocomplex to form. This was followed by the addition of Protein A and Protein G agarose, respectively for another two-hour incubation at room temperature which would allow for Protein A or Protein G to immunoprecipitate the plasminogen/PrP immunocomplex formed. The plasminogen present in anti-PrP immunoprecipitates was then detected on a Western blot using the anti-plasminogen antibody (FIG. 3).

In addition, immunoaffinity experiments showed that that there is a naturally occurring interaction between plasminogen and prion protein (FIG. 3). These results illustrate the capability of separating and concentrating the prion protein from blood fractions.

Human Plasma Prion Separation and Concentration

To investigate the capability of membrane-based electrophoresis to remove prions during purification process of plasma products, a partitioning study was performed by spiking bovine prion protein into human plasma. Complete prion clearance of the original spike was achieved during the purification of human albumin, immunoglobulin and α1-proteinase inhibitor by membrane-based electrophoresis. Embodiments practiced according to the claims remove causative TSE agents during plasma fractionation, thus eliminating the risk of prion disease transmission.

EXAMPLE 3

Size Based Separation

Size-based separation of PrPc was carried out for 2 hours at 250V using Tris Borate buffer (20 mM Boric Acid, 45 mM Trizma Base, pH 9.0) as the running buffer. All cartridge set ups involved the use of two restriction membranes with a molecular mass cut-off of about 10 kDa and a separation membrane of varying molecular mass cut-offs ranging from 100 kDa to 1000 kDa, respectively.

The results of initial experiments described above are shown in Table 1 and FIG. 4.

TABLE 1

Size-based separation of PrPc from normal human plasma.

| Run | Cartridge | Starting material | Stream 1 (% of total starting PrP) | Stream 2 (% of total starting PrP) |
|---|---|---|---|---|
| 1 | 10-100-10 | Plasma | 115 | * |
| 3 | 10-200-10 | Plasma | 80 | 10 |
| 5 | 10-800-10 | Plasma | 53 | 25 |
| 7 | 10-1000-10 | Plasma | * | 58 |

* Below limit of detection

Figure 4:
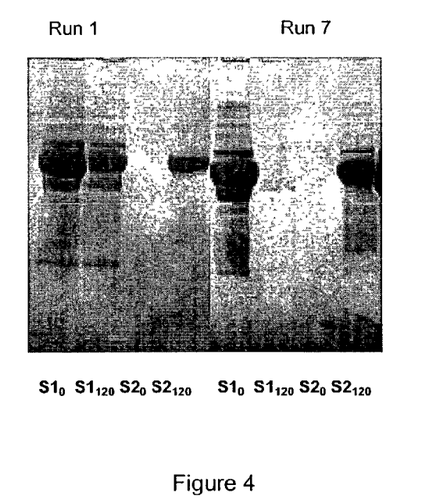
FIG. 4 is an SDS-PAGE analysis of $PrP^c$ from normal human plasma in electrophoresis run number 1 & 7 as described in Example 3 and Table 1. Lanes $S1_0$ is Stream 1 at time 0 minutes, $S1_{120}$ is Stream 1 at time 120 minutes, $S2_0$ is Stream 2 at time 0 minutes, $S2_{120}$ is Stream 2 at time 120 minutes of run 1, respectively. Lanes $S1_0$ is Stream 1 at time 0 minutes, $S1_{120}$ is Stream 1 at time 120 minutes, $S2_0$ is Stream 2 at time 0 minutes, $S2_{120}$ is Stream 2 at time 120 minutes of run 7, respectively.
Figure 5:
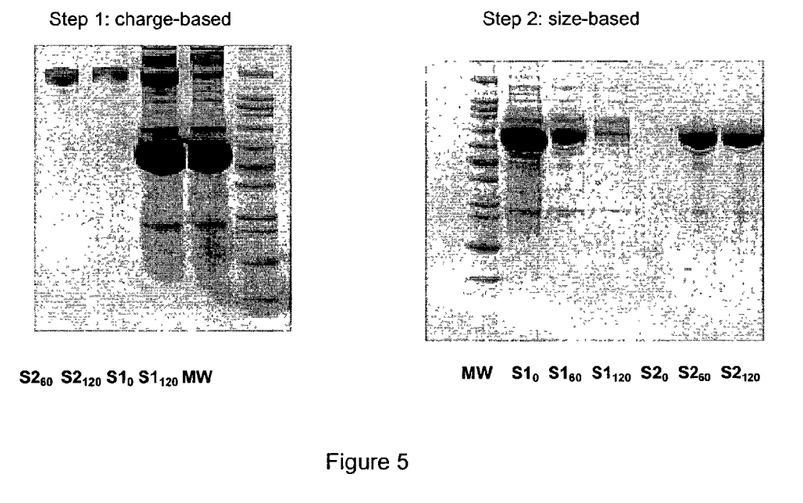
FIG. 5 is an SDS PAGE analysis of charge-based separation of $PrP^c$ from normal human plasma using a Large-type separation membrane having a molecular mass cut-off of 1000 kDa (step 1), followed by a size-based separation using Small-type separation membrane having a molecular mass cut-off of 200 kDa (step 2), as described in Example 4 and Table 2.
Figure 6:
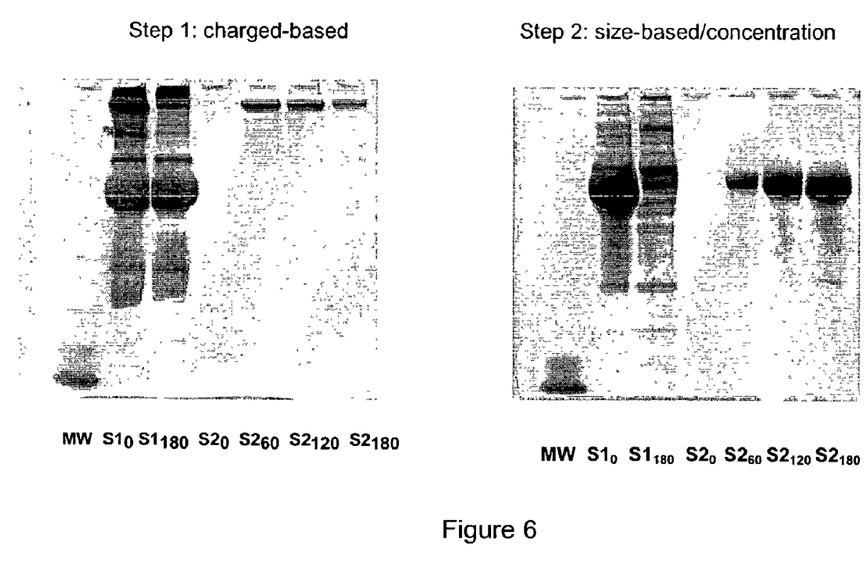
FIG. 6 shows SDS PAGE analysis of charge-based separation of $PrP^c$ from normal human plasma using a Large-type separation membrane having a molecular mass cut-off of 1000 kDa (step 1), followed by a size-based separation using Small-type separation membrane having a molecular mass cut-off of 200 kDa and a PVA membrane as an upper restriction membrane (step 2), as described in Example 5.

FIG. 4 shows the results of a SDS-PAGE analysis of the electrophoresis run number 1 and 7. Lanes 1, 2, 3, 4 are S1 0 minutes, S1 120 minutes, S2 0 minutes, S2 120 minutes of run 1, respectively. Lanes 5, 6, 7, 8: S1 0 minutes, S1 120 minutes, S2 0 minutes, S2 120 minutes of run 7, respectively. From the analysis of the electrophoretic runs, it was evident that low molecular weight proteins came through the smallest-type separation membrane with a molecular mass cut-off of about 100 kDa, while the use of the large-type separation membrane with a molecular mass cut-off of about 1000 kDa resulted in the complete transfer of albumin and other high molecular weight proteins from the samples.

EXAMPLE 4

Charge-Based Separation

Charged-based separation of $PrP^c$ was carried out for 2 hours at 250V using a cartridge set up consisting of two restriction membranes with a molecular mass cut-off of about 10 kDa and a large-type separation membrane with a molecular mass cut-off of about 1000 kDa. Different buffers used were in the range pH 4.8 to pH 9.0. For all of the runs listed in Table 2, normal human plasma was used as the starting material and the source of $PrP^c$.

TABLE 2

Charge-based separation using a LARGE-type separation membrane

| Run | Buffer pH | Polarity | Stream 1 (% of total starting PrP) | Stream 2 (% of total starting PrP) |
|---|---|---|---|---|
| 10 | MES/β-Alanine pH 4.8 | Reverse | 67 | * |
| 11 | MOPS/GABA pH 5 | Forward | 40.2 | 13.5 |
| 14 | Hepes/Imidazole pH 6 | Forward | 53 | 10 |
| B08 | MOPS/β-Alanine pH 6.5 | Forward | 44.7 | 13.1 |
| 15 | Hepes/Imidazole pH 7 | Forward | 19.5 | 39.2 |
| 16 | Tris/Borate pH 8 | Forward | 56 | 10 |
| B14 | Tris/Borate pH 8.5 | Forward | 19.6 | 38.6 |
| 17 | Tris/Borate pH 9 | Forward | * | 58 |

* Below limit of detection

Using human plasma as a starting material, size-based separation of normal prion protein was performed followed by a charge-based separation. The amount of prion protein in human plasma was quantified by a time-resolved dissociation-enhanced fluoroimmunoassay (DELFIA®). Results clearly indicate that membrane-based electrophoresis is able to purify and concentrate prion protein from human plasma. Membrane-based electrophoresis has, therefore, the capability for not only abnormal prion protein separation but also enrichment prior to a suitable detection assay.

A two step separation process of $PrP^c$ was performed in order to achieve isolation of $PrP^c$ from the majority of normal human plasma proteins. First step separation (a charge-based separation) of $PrP^c$ was carried out in reverse polarity for 2 hours at 250V using MOPS/GABA buffer (80 mM MOPS, 20 mM GABA, pH 5.0) as the running buffer. The anode was positioned adjacent stream 1 and the cathode positioned adjacent stream 2 (reverse polarity configuration). The plasma sample was placed in stream 1 and subjected to electrophoresis. The electrophoresis cartridge consisted of two restriction membranes with a molecular mass cut-off of about 10 kDa and a large-type separation membrane having a molecular mass cut-off of about 1000 kDa positioned between the restriction membranes. Both high and low molecular weight proteins with pI values greater than 5.0 were moved from the sample in stream 1 to stream 2 and the partially purified $PrP^c$ remained in stream 1. The PrP fraction was then used as the starting material for the second step.

Second step separation (a size-based separation) of $PrP^c$ was carried out in forward polarity for 2 hours at 250V using Tris Borate buffer (20 mM Boric Acid, 45 mM Trizma Base, pH 9.0) as the running buffer. The cathode was positioned adjacent stream 1 and the anode positioned adjacent stream 2 (normal polarity configuration). The PrP fraction from the first step was placed in stream 1 and subjected to electrophoresis. The electrophoresis cartridge set up consisted of two restriction membranes with a molecular mass cut-off of about 10 kDa and a small-type separation membrane with a molecular mass cut-off of about 200 kDa. Low molecular weight proteins with pI values less than 9.0 were removed to stream 2 while $PrP^c$ was fully retained in stream 1. (As previously shown in Table 1 and FIG. 4, Run 1, a size-based separation with a 200 kDa separation membrane can retain the majority of plasma $PrP^c$ in Stream 1 whereas the low molecular weight plasma protein contaminants (e.g., Albumin) were moved to Stream 2).

The two-step separation protocol resulted in removal of contaminant proteins with pI values between 5 to 9 (90% Albumin, 80% IgG, 100% 1-proteinase inhibitor removed). Results of the separation using step 1 and step 2 are shown in FIG. 5.

Simultaneous Separation and Concentration of Human Plasma PrP

EXAMPLE 5

The electrophoresis cartridge set up from the second step of the two-step separation process (described above), was modified such that the upper restriction membrane which forms part of stream 1 was replaced with a polyvinyl-alcohol membrane (PVA) (endosmosis membrane) in order to achieve a simultaneous separation and concentration of PrP. FIG. 6 shows an SDS PAGE analysis of a charge-based separation using a Large-type separation membrane having a molecular mass cut-off of 1000 kDa (step 1), followed by a size-based separation using Small-type separation membrane having a molecular mass cut-off of 200 kDa and a PVA membrane as an upper restriction membrane (step 2). At the end of the separation process, a 3 fold increase in the concentration of PrP was achieved based on the quantitative DELFIA analysis. A variety of other endosmotic membranes may be used including cellulose triacetate (CTA).

Bovine Prion Separation and Concentration

EXAMPLE 6

Figure 7:
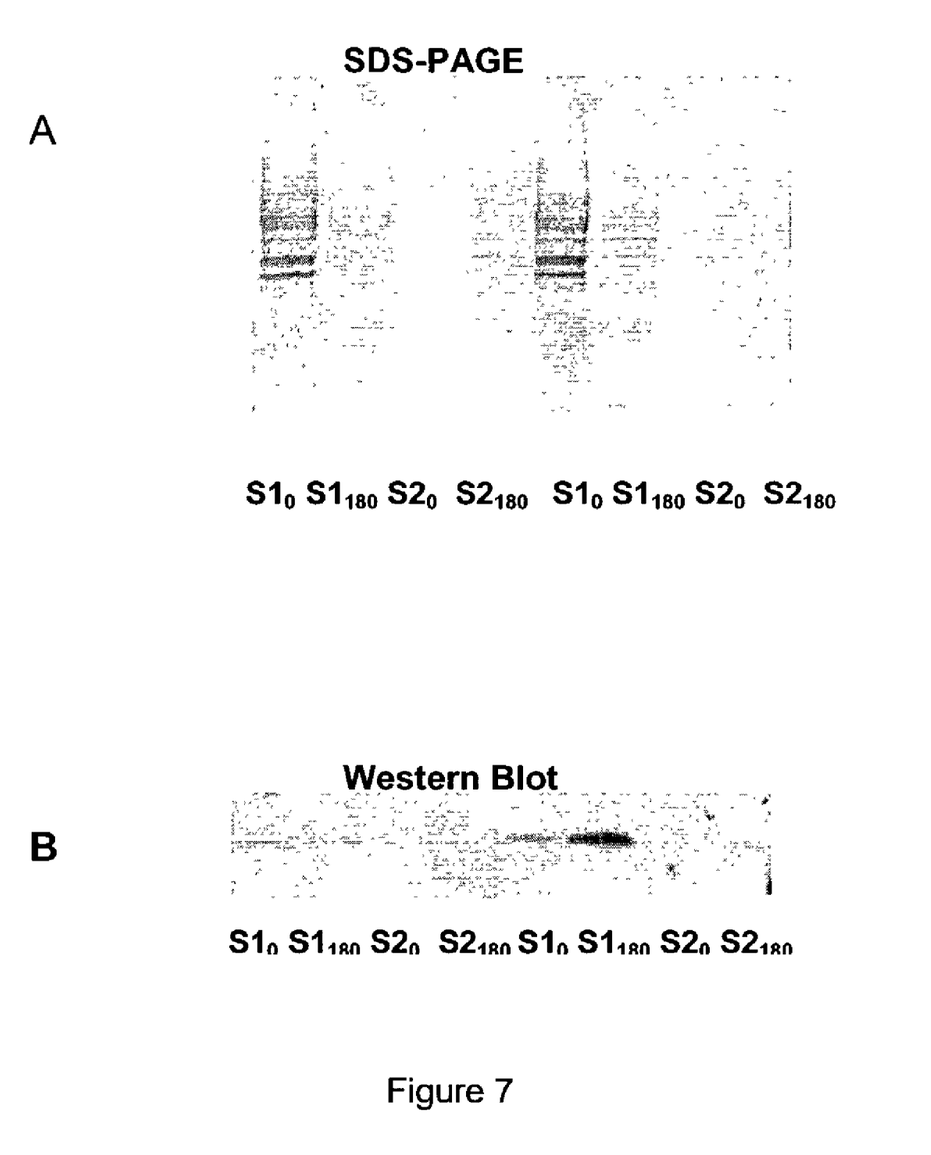
FIG. 7 shows analysis of simultaneous separation and concentration of the bovine prion protein (PrP) from bovine brain homogenate using membrane-based electrophoresis technology and the PVA membrane as described in Example 6. Panel A: SDS-PAGE of the samples from the electrophoresis run; Panel B: Western blot of the samples from the electrophoresis run using anti-PrP R029; $S1_0$ Stream 1 at time 0 minutes; $S1_{180}$ Stream 1 at time 180 minutes.

FIG. 7 shows the results of simultaneous separation and concentration of the bovine prion protein (PrP) from bovine brain homogenate using membrane-based electrophoresis technology and a PVA membrane. Panel A 
(c) supplying sample or liquid from at least the first sample reservoir to the first sample chamber, or from the second sample reservoir to the second sample chamber; and (d) detecting the presence of the concentrated prions by an immuno-detection assay selected from the group consisting of an enzyme linked immunosorbant assay, Western Blot, time-resolved dissociation-enhanced fluoroimmunoassay (DELFIA), and wherein the first ion-permeable barrier is an electrophoresis membrane having a molecular mass cut-off of about 1000 kDa and the second and the third ion-permeable barriers are restriction membranes having a molecular mass cut-off of about 10 kDa; and (b) detecting the presence of the separated or concentrated prions.

6. A method for detecting prions in a sample comprising:
(a) subjecting a sample to membrane-based electrophoresis in an electrophoresis apparatus to separate or concentrate at least some prions present in the sample, the electrophoresis apparatus comprising
  (i) a separation unit having a first electrolyte chamber and a second electrolyte chamber in fluid connection with an electrolyte reservoir, a first sample chamber being in fluid connection with a first sample reservoir, and a second sample chamber being in fluid connection with a second sample reservoir;
  (ii) a first ion-permeable barrier positioned between the first sample chamber and the second sample chamber, wherein the first ion-permeable barrier minimizes convective mixing of contents of the first and second sample chambers;
  (iii) a second ion-permeable barrier positioned between the first electrolyte chamber and the first sample chamber, wherein the second ion-permeable barrier minimizes convective mixing of contents of the first electrolyte chamber and the first sample chamber; and
  (iv) a third ion-permeable barrier positioned between the second sample chamber and the second electrolyte chamber, wherein the third ion-permeable barrier minimizes convective mixing of contents of the second electrolyte chamber and the second sample chamber,
wherein the first ion-permeable barrier is an electrophoresis membrane having a molecular mass cut-off of about 1000 kDa, the second ion-permeable barrier is an inducible electro-endo-osmotic membrane, and the third ion-permeable barrier is a restriction membrane having a molecular mass cut-off of about 10 kDa; and (b) detecting the presence of the separated or concentrated prions.

7. The method according to claim 5 or 6, wherein the sample is a biological sample selected from the group consisting of whole blood, plasma, serum, cell products, cell extracts, cerebrospinal fluid, tissue homogenates, urine, semen, and combinations thereof.

8. The method according to claim 5 or 6, wherein the first ion-permeable barrier is an electrophoresis separation membrane formed from polyacrylamide.

9. The method according to claim 6, wherein the inducible electro-endo-osmotic membrane is formed from a polyvinyl alcohol or cellulose triacetate (CTA).

10. The method according to claim 5 or 6, wherein the separation unit is provided as a removable cartridge or cassette housing the ion-permeable barriers.

11. The method according to claim 5 or 6, wherein the contents from each of the first and second sample reservoirs are circulated through the first and second sample chambers.

12. The method according to claim 5 or 6, wherein the electrophoresis apparatus contains a pump arrangement.

13. The method according to claim 12, wherein the pump arrangement contains a peristaltic pump.

14. The method according to claim 5 or 6, wherein the electrophoresis apparatus removes and replaces sample in the first or second sample reservoirs.

15. The method according to claim 5 or 6, wherein the electrophoresis apparatus contains a cooling arrangement.

16. The method according to claim 15, wherein the electrophoresis apparatus maintains the temperature of the electrolyte and the sample solution.

17. The method according to claim 5 or 6, wherein the detecting step or the electrophoresis apparatus is automated.

18. The method according to claim 5 or 6, wherein step (b) is a prion capture system utilizing a selective binding agent.

19. The method according to claim 18, wherein the selective binding agent is a biological or chemical agent which selectively binds prions.

20. The method according to claim 19, wherein the selective binding agent preferentially binds infectious prions.

21. The method according to claim 19, wherein the biological agent is selected from the group consisting of a protein, peptide or other small molecule, antibody, binding fragment of an antibody, plasminogen, fibrin, and fibrinogen.

22. The method according to claim 19, wherein the chemical agent is a heteropoly acid or salts thereof.

23. The method according to claim 22, wherein the heteropoly acid is phosphotungstic acid or salts thereof.

24. The method according to claim 5 or 6 wherein step (b) further comprises detecting and identifying infectious prions.

25. The method according to claim 5 or 6, further comprising:
  (c) characterizing physical or biochemical properties of the detected prions.

26. The method according to claim 25, wherein the characterizing step is performed by measuring the solubility, three-dimensional structure, circular dichroism (CD), phydrophobicity, infectivity or pI value of the detected prions.

27. The method according to claim 5 or 6, wherein step (a) further comprises:
  concentrating at least some prions into a smaller volume.

* * * * *